United States Patent [19]

Tokushige et al.

[11] 3,959,357

[45] May 25, 1976

[54] METHOD FOR CONTINUOUSLY THERMALLY DECOMPOSING SYNTHETIC MACRO-MOLECULE MATERIALS

[75] Inventors: Hiroyuki Tokushige; Akira Kosaki; Tadamoto Sakai, all of Hiroshima, Japan

[73] Assignee: Japan Steel Works, Ltd., Japan

[22] Filed: Dec. 12, 1974

[21] Appl. No.: 532,064

Related U.S. Application Data

[63] Continuation of Ser. No. 335,309, Feb. 23, 1973, abandoned.

[52] U.S. Cl. .............................. 260/486 R; 260/2.3; 260/465.9; 260/669 R; 260/676 R; 260/683 R
[51] Int. Cl.² ........................................ C07C 69/54
[58] Field of Search ......... 260/486 R, 465.9, 669 R, 260/676 R, 683 R

[56] References Cited
UNITED STATES PATENTS

| | | | |
|---|---|---|---|
| 2,030,901 | 2/1936 | Strain | 260/486 R |
| 2,341,282 | 2/1944 | Marks | 260/486 R |
| 2,377,952 | 6/1945 | Marks | 260/486 R |

*Primary Examiner*—Paul J. Killos
*Attorney, Agent, or Firm*—McGlew and Tuttle

[57] ABSTRACT

Synthetic macro-molecule materials are continuously supplied into the cylinder of an extruder so that said synthetic macro-molecule materials are internally heated by the shearing as well as kneading action of the screw to which they are subjected and externally heated by the heat transmitted through the wall of the cylinder of said extruder from an outside heat source so that said synthetic macro-molecule materials are continuously thermally decomposed within said cylinder, thereby vapourized thermally decomposed products are fed to the condensing means through one or more discharge orifices provided in said cylinder to be recovered there as thermally decomposed products having low molecular weights.

4 Claims, 2 Drawing Figures

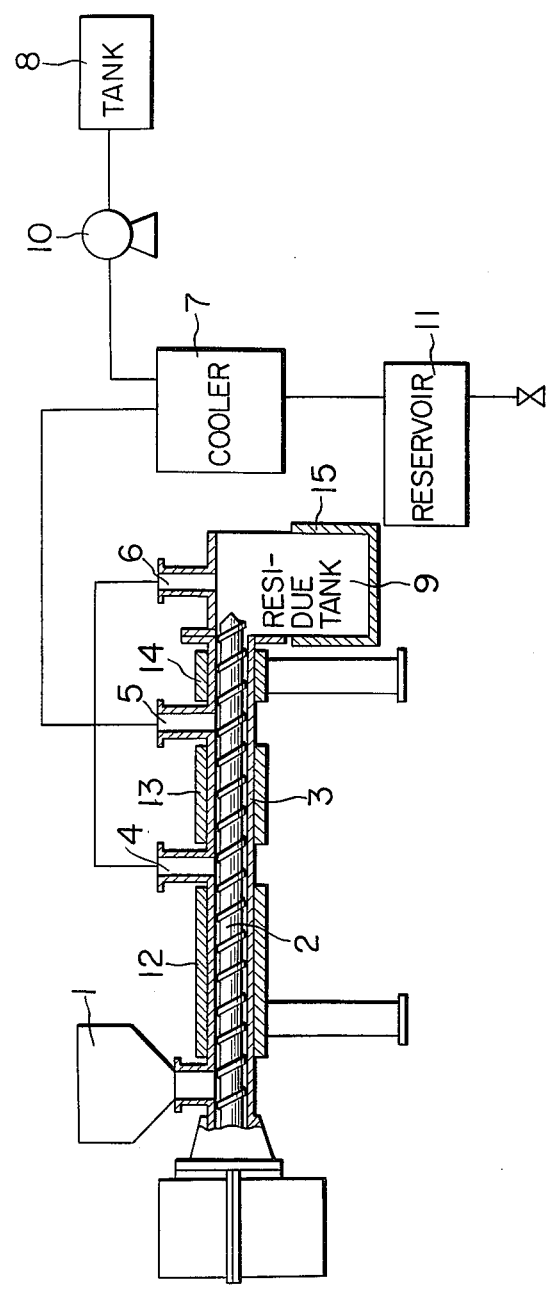

METHOD FOR CONTINUOUSLY THERMALLY DECOMPOSING SYNTHETIC MACRO-MOLECULE MATERIALS

This is a continuation of application Ser. No. 335,309 filed Feb. 23, 1973 now abandoned.

BACKGROUND OF THE INVENTION

The present invention relates to a method for continuously thermally decomposing synthetic macro-molecule materials and more particularly to a method for continuously thermally decomposing synthetic macro-molecule materials to recover the vaporized thermally decomposed products having low molecular weights by heating said synthetic macro-molecule materials to their thermal decomposition temperature.

As systems for thermally decompose the synthetic macro-molecule materials in order to obtain products having low molecular weights, there have hitherto been known a batch-type and a continuous-type systems, but both of them have the following problems as common phenomena:

1. Since the synthetic marco-molecule materials have a poor thermal conductivity, it requires a long time before reaching the thermal decomposition temperature, as the result of which the processing capacity for the thermal decomposition is small compared with the dimensions of the decomposition apparatus;

2. Most of the snythetic macro-molecule materials contain substances hard to be thermally decomposed such as inorganic fillers, etc. and moreover carbon compounds remain as the residue of the thermal decomposition. These carbon residues have a tendency to firmly adhere to the walls of the thermal decomposition apparatus and, in most cases, it is difficult to continuously discharge them from the apparatus;

3. Many of the synthetic macro-molecule materials become melts having high viscosity in the process of heating, so that their transportation becomes difficult.

SUMMARY OF THE INVENTION

It is an object of the present invention to provide a method for continuously thermally decomposing synthetic macro-molecule materials which can eliminate all of such difficulties as abovesaid, which are inherent to the conventional methods.

A method for continuously thermally decomposing synthetic macro-molecule materials according to the present invention is characterized to supply said synthetic macro-molecule materials into the cylinder of an extruder having a screw which functions to shear, knead and transport said synthetic macro-molecule materials so that they are continuously thermally decomposed by internal heat generated by the shearing and kneading action to which they are subjected as well as by the external heat transmitted through the wall of said cylinder which is heated by an external heat source, thereby the volatilized thermo-decomposed products are discharged through one or more discharge orifices provided in the cylinder of said extruder to the condensing means to recover the material there. As the extruder a single-screw type or a twin-screw type of any known construction may be used, either independently or in combinaton, such as using a single-screw type and a twin-screw type extruders in tandem, or in combination with any other apparatus.

BRIEF DESCRIPTION OF THE DRAWING

This and other objects of the present invention will become more readily apparent upon reading of the following specification and upon reference to the accompanying drawing, which shows diagrammatically a preferred apparatus for carrying out the method according to the present invention using a single-screw type extruder independently as the extruder.

DESCRIPTION OF THE PREFERRED EMBODIMENTS

Reference is made to the drawing.

The synthetic macro-molecule materials to be treated are supplied into a hopper 1. The synthetic marco-molecule materials thus supplied are fed forwardly by a rotating screw 2 to be plasticized and thermally decomposed by internal heat generated by their subjection to the shearing and kneading action of said screw as well as by the external heat transmitted through the wall of the cylinder 3 of said extruder which is heated by any suitable heating means 12, 13, 14 such as electric heaters. A fear of fire due to the back flow of the thermally decomposed products towards the hopper side can be prevented by sealing action of the melt during its transportation. Accordingly the feeding of the synthetic macro-molecule materials into hopper 1 can be carried out by any known means. However, in the case where there occurrs variation in supplying the synthetic macro-molecule materials due to such as the occurrence of bridging of the synthetic macro-molecule materials in hopper 1, the filling state of cylinder 3 with the melt may be insufficient, so it is preferable that hopper 1 is constructed so as to be replaced by nitrogen. The heating of cylinder 3 is preferable to be carried out separately at the melting zone and the thermal decomposition zone, making their temperatures, respectively, e.g. about 250°C and 500°–600° C.

Products having low molecular weights volatilized from the heated synthetic macro-molecule materials are led to a cooler 7 through discharge orifices 4–7 to be condensed there, the condensate being accumulated in a reservoir 11. The discharge orifices are appropriately provided in cylinder 3 over its whole length from the position at which the thermal decomposition starts to the forward end of cylinder 3. And when it is desired to return the product having high boiling points to cylinder 3 again for its further thermal decomposition, it is preferable to provide one of the discharge orifices at right angles to the thermal decomposition starting position. Further, in condensing the volatilized products, if the temperature of the cooler is adequately adjusted or a multi-stage distilling column or the like is used as the cooler, the refining of the thermal decomposition product can be accomplished at the same time with its thermal decomposition. Non-condensed ingredients of gases are stored in a tank 8.

Though the formation of the residue carbon may occur on the inner surface of the cylinder, its adhesion to the surface can be prevented by the thread of screw 3, but, in order that the residue formed is surely fed to a residue tank 9, it is necessary that screw 3 is provided with the thread extending to its forward end so that it projects into residue tank 8 which is directly connected to the extruder at its forward end.

Further, in this case, to further thermally decompose the material supplied in the incomplete decomposition state as the result of externally heating the residue tank to high thermal temperatures is adventageous when the supply amount of the material has increased beyond the thermally decomposing capacity of the cylinder due to some cause or in the case when treating such a material as needing a comparatively long period of time for its thermal decomposition up to a given mean molecular weight.

In the case when part of the residual carbon is liable to adhere to the flow passage of the screw, such a tendency can be alleviated by externally supplying a little amount of air into the thermal decomposing zone while the system is under operation, whereby the residual carbon becomes comparatively active making such residual carbon adherence difficult. In this case, as part of the product burns, it contributes toward reducing the amount of the external heating. Further, as a mechanism for supplying the residual carbon completely, it is desired that the whole of the cylinder or the thermally decomposing zone is constructed to use a two-shaft-engaging screw.

Further, in this case, since the products produced partially burn, contributing to reduce the quantity of the outer heating.

It is preferable to use twin-type screw for the whole extruder or only for the thermal decomposition zone in order to perfectly feed the residue.

When the necessity has occurred to perfectly remove the residue carbon firmly adhered to the flow passage of the screw after the continuous operation, it can be achieved by stopping the supply of the synthetic macromolecule materials and supplying air to the thermal decomposition zone so that the carbon firmly adhered is changed into carbon dioxide.

In the present invention, it is possible to control the mean molecular weight of the thermally decomposed products by regulating the degree of vacuum at the thermal decomposition zone by means of a vacuum pump 10 disposed at the end of the condensing part, this being especially advantageous in the treatment of the random decomposition type synthetic macromolecule materials, e.g. polyethylene etc. The control of the mean molecular weight of the thermally decomposed products can also be carried out by changing the thermal decomposition temperature or the feed velocity, the former being possible by changing the external heating temperature of the cylinder by the control of heaters, 12, 13, 14, while the latter is possible by changing the number of rotation of the screw.

Thus, according to the continuously thermally decomposing method of the present invention, it is possible to melt and thermally decompose rapidly and uniformly even synthetic macro-molecule materials of poor thermal conductivity by the internal heat produced by the application of shearing and the external heating, as well as, at the same time, it is possible to discharge the residue continuously on the strength of the transporting ability of the screw.

With the synthetic macro-molecule materials of such a random type as polyethylene, too, it is possible, according to the present invention, to adjust the degree of their thermal decomposition by controlling the feed velocity for the material, the temperatures for thermal decomposition and the degree of vacuum; and it is also possible to obtain low-molecular products in liquid type or wax-like, depending on decomposing conditions.

On the other hand, with the synthetic macromolecule materials which is easy to produce monomers by the thermal decomposition, the secondary reaction at the time of the thermal decomposition is less so that the monomers can be recovered with a large yield.

The following specific examples will serve to illustrate preferred embodiments of the invention, although it should be understood that these examples are not intended to limit the scope of the invention.

EXAMPLE 1

The experiment was made using a single-screw type extruder having an inner diameter of 40 mm.

The material was "polystyrene 525–51" (a trade name of Mitsui Toatsu Chemical Inc.) as the general polystyrene.

| Thermal Decomposition Temperature (°C) | Degree of Vacuum (Gauge Pressure; mm Hg) | Number of Rotation of Screw (r.p.m.) | Yield Ratio of Liquid Products (%) | Amount of Styrene in the Liquid (%) |
|---|---|---|---|---|
| 500°C | −50mm Hg | 30rpm | 96.7% | 74.5% |
| " | −250 | " | — | 80.9 |
| " | −500 | " | 96.0 | 79.0 |
| 600 | Atmosphere | 40 | 97.0 | 72.8 |
| " | −50mm Hg | " | 100.0 | 77.3 |
| " | −250 | " | 99.5 | 81.6 |
| " | −500 | " | 98.0 | 79.4 |

The most of the recovered liquid decomposed products was styrene together with dimer, trimer, toluene, benzene, α-methyl styrene.

In this case, the formation of the residue carbon was not recognized at all, but the gaseous decomposed products was about 0.5–4.0%.

EXAMPLE 2

The experiment was made using a single-screw extruder having an inner diameter of 40 mm.

The material was "High Impact Polystyrene 830–02" (a trade name of Mitsui Toatsu Chemical, Inc.) as anti impact polystylene.

| Thermal Decomposition Temperature (°C) | Degree of Vacuum (Gauge Pressure; mm Hg) | Number of Rotation of Screw (r.p.m.) | Yield Ratio of Liquid Products (%) | Amount of Styrene in the Liquid (%) |
|---|---|---|---|---|
| 500°C | −50mm Hg | 30rpm | 97.1% | 76.2% |
| " | −500 | " | 95.7 | 74.1 |
| " | −650 | " | 95.7 | 79.5 |
| 600 | Atmosphere | 60 | 78.0 | 89.3 |
| " | −250 | " | 96.5 | 76.0 |
| " | −500 | " | 97.9 | 78.6 |

The most of the liquid products was stylene. The gaseous products were somewhat more than the case of the general polystyrene and inflammable. The thermal decomposed residue carbon was about 1–2% and most of it was recovered from the residue tank, but a small amount of the carbon was recognized in the flow passage of the screw.

EXAMPLE 3

The experiment was made using a single-screw type extruder having an inner diameter of 40 mm.

The material was "Cyco Lac T1100" (a trade name of Ube Cycom Co., Ltd.) as the copolymer of acrylonitrile, butadiene and stylene.

| Temperature (°C) | (Gauge Pressure; mm Hg) | Rotation of Screw (r.p.m.) | Products (%) | in the Liquid (%) |
|---|---|---|---|---|
| 500°C | −100mm Hg | 50rpm | 67.8% | 51% |
| 600 | " | " | 88.8 | 44 |

The liquid products included a relatively large quantity of styrene, but acrylonitrile, toluene, α-methyl styrene, etc. are also recognized. Further, in the gaseous products the existence of ammonia was not recognized. Though, when the thermal decomposition temperature was not equilibrated with the material supply velocity (i.e. r.p.m. of the screw), the thermal decomposition in the extruder did not completed so that incompletely thermally decomposed products were fed into the residue tank, the thermal decomposition was completed by heating the residue tank.

EXAMPLE 4

The experiment was made using a single-screw type extruder having an inner diameter of 40 mm.

The material was "Shinko Lac, ABS" (a trade name of Mitsubishi Rayon Co., Ltd.) as polymethylmethacrylate.

| Thermal Decomposition Temperature (°C) | Degree of Vacuum (Gauge Pressure; mm Hg) | Number of Rotation of Screw (r.p.m.) | Yield Ratio of Liquid Products (%) |
|---|---|---|---|
| 500°C | −100mm Hg | 50rpm | 99.6% |
| " | −250 | " | 97.0 |

More than 95% of the liquid products was methyl methacrylate monomer.

Further, in this case, the formation of carbon after the thermal decomposition was not recognized at all.

EXAMPLE 5

The experiment was made using a single-screw type extruder having an inner diameter of 40 mm.

The material was "Poly Propylene F600" a trade name of Mitsui Petrochemical Industries, Ltd.) as polyplopylene.

| Thermal Decomposition Temperature (°C) | Degree of Vacuum (Gauge Pressure; mm Hg) | Number of Rotation of Screw (r.p.m.) | Yield Ratio of Liquid Products (%) | Properties of Products |
|---|---|---|---|---|
| 600°C | Atmosphere | 40rpm | 70.0% | Liquidous at a room temperature |
| " | −100mm Hg | " | 68.5 | " |
| " | −250 | 50 | 72.5 | Greasy at a room temperature |

The thermally decomposed products varied from a liquidous substance of low viscosity at a room temperature to a greasy one according to the decomposition condition.

The gaseous products were obtained in the amount of 20% or thereabout, and their property corresponded to that of LPG. Further no carbon produced by the thermal decomposition was recognized in this experiment.

EXAMPLE 6

The experiment was made using a single-screw type extruder having an inner diameter of 40 mm.

The material was "Mirason Neo 23H" (a trade name of Mitsui Porichemical Industries, Ltd.) as polyethylene.

| Thermal Decomposition Temperature (°C) | Degree of Vacuum (Gauge Pressure; mm Hg) | Number of Rotation of Screw (r.p.m.) | Yield Ratio of Liquid Products (%) | Properties of Products |
|---|---|---|---|---|
| 600°C | Atmosphere | 20rpm | 66.0% | Liquidous at a room temperature |
| " | " | 40 | 76.0 | " |
| " | −100mm Hg | " | 80.0 | Greasy at a room temperature |

The thermally decomposed products obtained varied from a liquid-like substance with low viscosity at a room temperature to a greasy one or a wax-like one according to the decomposition condition.

As the result of the analysis of the thermally decomposed products by a gas chromatography, hydrocarbon having carbons in number ranging from 5 to about 35 were obtained.

The decomposition condition effected remarkably on the mean value of number of carbon rather than the range of the distribution of the carbon. The gaseous products were inflammable gasses comprising principally ethylene and propylene.

What is claimed is:

1. Method for continuously thermally decomposing a synthetic macro-molecule composition consisting essentially of an organic polymer selected from the group consisting of polystyrene; copolymer of acrylonitrile, butadiene and styrene; polymethylmethacrylate; polypropylene; and polyethylene, comprising the steps of continuously supplying said synthetic macro-molecule composition in an extruder and having a cylinder with means for heating said composition to a temperature of from 500°C to 600°C and discharge orifices for removing volatile products, said extruder being capable of subjecting said synthetic macro-molecule composition to shearing and kneading, transporting said synthetic macro-molecule composition within said extruder and continuously shearing and kneading said composition, continuously heating and thermally decomposing said synthetic macro-molecule composition in said cylinder of said extruder at a temperature from about 500°C to about 600°C, discharging low molecular weight volatilized products of not more than about 35 carbon atoms from thermally decomposing said composition through said discharge orifices in said cylinder of said extruder, conveying said low molecular weight volatilized products of not more than about 35 carbon atoms to condensing means directly connected to said discharge orifices, and condensing said low molecular weight volatilized products in said condensing means as products having from about 5 to about 35 carbon atoms per molecule.

2. Method for continuously thermally decomposing synthetic macro-molecule composition as claimed in claim 1, wherein said condensing means are provided with means for reducing pressure and providing a vacuum therein, whereby the mean molecular weight of said low molecular weight products to be recovered is controlled by controlling the degree of vacuum in said condensing means.

3. Method for continuously thermally decomposing synthetic macro-molecule composition as claimed in claim 1, wherein the residue of said synthetic macro-molecule materials having not been decomposed in the cylinder of said extruder is discharged at the discharge end of said extruder into a residue receiving means directly connected to said end by the screw of said extruder, said screw having one or more threads projecting into said residue receiving means.

4. Method for continuously thermally decomposing synthetic macro-molecule composition, according to claim 1, wherein the melting of the said synthetic macro-molecule composition is carried out in said cylinder in a melting zone at about 250°C.

* * * * *